(12) United States Patent
Barthe et al.

(10) Patent No.: US 7,571,336 B2
(45) Date of Patent: Aug. 4, 2009

(54) METHOD AND SYSTEM FOR ENHANCING SAFETY WITH MEDICAL PERIPHERAL DEVICE BY MONITORING IF HOST COMPUTER IS AC POWERED

(75) Inventors: Peter G Barthe, Phoenix, AZ (US); Michael H Slayton, Tempe, AZ (US); Vadim Kouklev, Tempe, AZ (US); Paul M Jaeger, Mesa, AZ (US)

(73) Assignee: Guided Therapy Systems, L.L.C., Mesa, AZ (US)

( * ) Notice: Subject to any disclaimer, the term of this patent is extended or adjusted under 35 U.S.C. 154(b) by 469 days.

(21) Appl. No.: 11/380,161

(22) Filed: Apr. 25, 2006

(65) Prior Publication Data

US 2006/0282691 A1 Dec. 14, 2006

Related U.S. Application Data

(60) Provisional application No. 60/674,964, filed on Apr. 25, 2005.

(51) Int. Cl.
 *G06F 1/26* (2006.01)
(52) U.S. Cl. .......................... 713/340; 607/5
(58) Field of Classification Search ................. 713/340, 713/300; 607/5
 See application file for complete search history.

(56) References Cited

U.S. PATENT DOCUMENTS

| | | | |
|---|---|---|---|
| 5,540,235 A | | 7/1996 | Wilson |
| 5,575,807 A | * | 11/1996 | Faller ............................. 607/5 |
| 5,615,091 A | | 3/1997 | Palatnik |
| 6,665,806 B1 | | 12/2003 | Shimizu |
| 2002/0040442 A1 | | 4/2002 | Ishidera |
| 2003/0200481 A1 | | 10/2003 | Stanley |
| 2004/0143297 A1 | * | 7/2004 | Ramsey, III .................... 607/5 |
| 2007/0032784 A1 | | 2/2007 | Gliklich et al. |

FOREIGN PATENT DOCUMENTS

DE 4029175 3/1992

OTHER PUBLICATIONS

International Search Report Dated Apr. 30, 2007.

* cited by examiner

*Primary Examiner*—Thomas Lee
*Assistant Examiner*—Albert Wang
(74) *Attorney, Agent, or Firm*—Snell & Wilmer L.L.P.

(57) ABSTRACT

A method and system for enhancing computer peripheral safety is provided. In accordance with various aspects of the present invention, the exemplary method and system are configured to monitor and/or isolate alternating current (A.C.) supplies with and/or from any peripheral subsystems or devices. An exemplary method and system comprises an A.C. supply, a host computer system, and a peripheral subsystem or device connected to the host computer system, such as an ultrasound imaging and/or therapy peripheral, and an isolation subsystem configured for monitoring and/or isolating the A.C. supply from the peripheral subsystem or device. In accordance with an exemplary embodiment, an isolation subsystem comprises application software and associated modules and functions that when executed continuously monitors and/or polls the host computer's hardware and/or operating system for the presence of an isolated source, such as a battery, or an unisolated power source, such as through a battery charger and/or other connection path to the A.C. main supply. In accordance with other exemplary embodiments, an isolation subsystem can comprises a wireless or other safe/isolated electrical link for connecting a patient contact device, and/or a verification link or other verification mechanisms configured between an isolation transformer and host computer to monitor or observe usage to power the host computer and peripheral subsystem.

22 Claims, 12 Drawing Sheets

METHOD AND SYSTEM FOR ENHANCING SAFETY WITH MEDICAL PERIPHERAL DEVICE BY MONITORING IF HOST COMPUTER IS AC POWERED

CROSS-REFERENCE TO RELATED APPLICATIONS

This application claims priority to U.S. Provisional Application No. 60/674,964, filed on Apr. 25, 2005 and entitled "Method And System For Enhancing Computer Peripheral Safety."

FIELD OF INVENTION

The present invention relates to computer peripherals and in particular to a method and system for enhancing electrical safety of peripheral systems and devices, such as those used for medical applications.

BACKGROUND OF THE INVENTION

Personal computers, or PCs, have become ubiquitous and exist in forms such as desktop, notebook (laptop), or several ultra-portable configurations among others. This pervasiveness has led to the development of a large assortment of increasingly sophisticated peripherals. In general, computer peripherals are devices that connect to a computing system to facilitate certain tasks and/or implement features not contained within the standard or base computer, including medical devices and other like equipment. However, the stringent electrical safety requirements and regulations which exist for medical equipment has circumscribed their use with PCs as peripherals. For example, electrical leakage currents must be severely limited to maintain patient isolation, yet computers and their peripherals are not commonly designed to accommodate such restrictions. One approach to alleviate these requirements is to employ an isolation transformer to power the computer and peripherals, but such a solution is expensive, bulky in size and weight, and relatively unsuited to portability. An alternative of custom-made power supplies is impractical, since a manufacturer of peripherals cannot design isolated power supplies for all conceivable PCs. What is needed is an effective means of providing computer peripheral safety.

SUMMARY OF THE INVENTION

A method and system for enhancing computer peripheral safety is provided. In accordance with various aspects of the present invention, the exemplary method and system are configured to monitor and/or isolate alternating current (A.C.) supplies with and/or from any peripheral subsystems or devices. An exemplary method and system comprises an A.C. supply, a host computer system, and a peripheral subsystem or device connected to the host computer system, such as an ultrasound imaging and/or therapy peripheral, and an isolation subsystem configured for monitoring and/or isolating the A.C. main supply from the peripheral subsystem or device.

In accordance with an exemplary embodiment, an isolation subsystem comprises application software and associated modules and functions that when executed continuously monitors and/or polls the host computer's hardware and/or operating system for the supply of power from an isolated power source, such as a battery supply, or from an unisolated power source, such as connection through a battery charger and/or other connection path to the A.C. main supply. If a connection to the A.C. main supply is detected, the application software shuts down or otherwise isolates the peripheral subsystem, thereby disallowing usage on a patient, and/or provides suitable warnings to a system user, such as requiring confirmation that an isolation subsystem/hardware is connected or operating. In accordance with an exemplary embodiment, the application software can also comprise A.C. detection modules configured to monitor the state of A.C. or battery power, to monitor the battery level, and give appropriate warnings and guidance to the user to facilitate control of any peripheral hardware or devices.

In accordance with another exemplary embodiment, an isolation subsystem comprises a wireless or other safe/isolated electrical link for connecting a patient contact device, such as a medical probe, to the peripheral subsystem to assure a high degree of isolation between the patient and electronics.

In accordance with another exemplary embodiment, an isolation subsystem comprises a verification link or other verification mechanisms configured between an isolation transformer and host computer to monitor or observe usage to power the host computer and peripheral subsystem.

BRIEF DESCRIPTION OF THE DRAWINGS

The subject matter of the invention is particularly pointed out in the concluding portion of the specification. The invention, however, both as to organization and method of operation, may best be understood by reference to the following description taken in conjunction with the accompanying drawing figures, in which like parts may be referred to by like numerals.

DETAILED DESCRIPTION

The present invention may be described herein in terms of various functional components and processing steps. It should be appreciated that such components and steps may be realized by any number of hardware components and software features configured to perform the specified functions. For example, the present invention may employ various medical treatment devices, visual imaging and display devices, input terminals and the like, which may carry out a variety of functions under the control of one or more control systems or other control devices. In addition, the present invention may be practiced in any number of computer peripheral contexts and that the exemplary embodiments relating to a method for enhancing computer peripheral safety as described herein for medical probes and applications are merely indicative of exemplary applications for the invention. For example, the principles, features and methods discussed may be applied to any computer application and peripheral.

Figure 1:
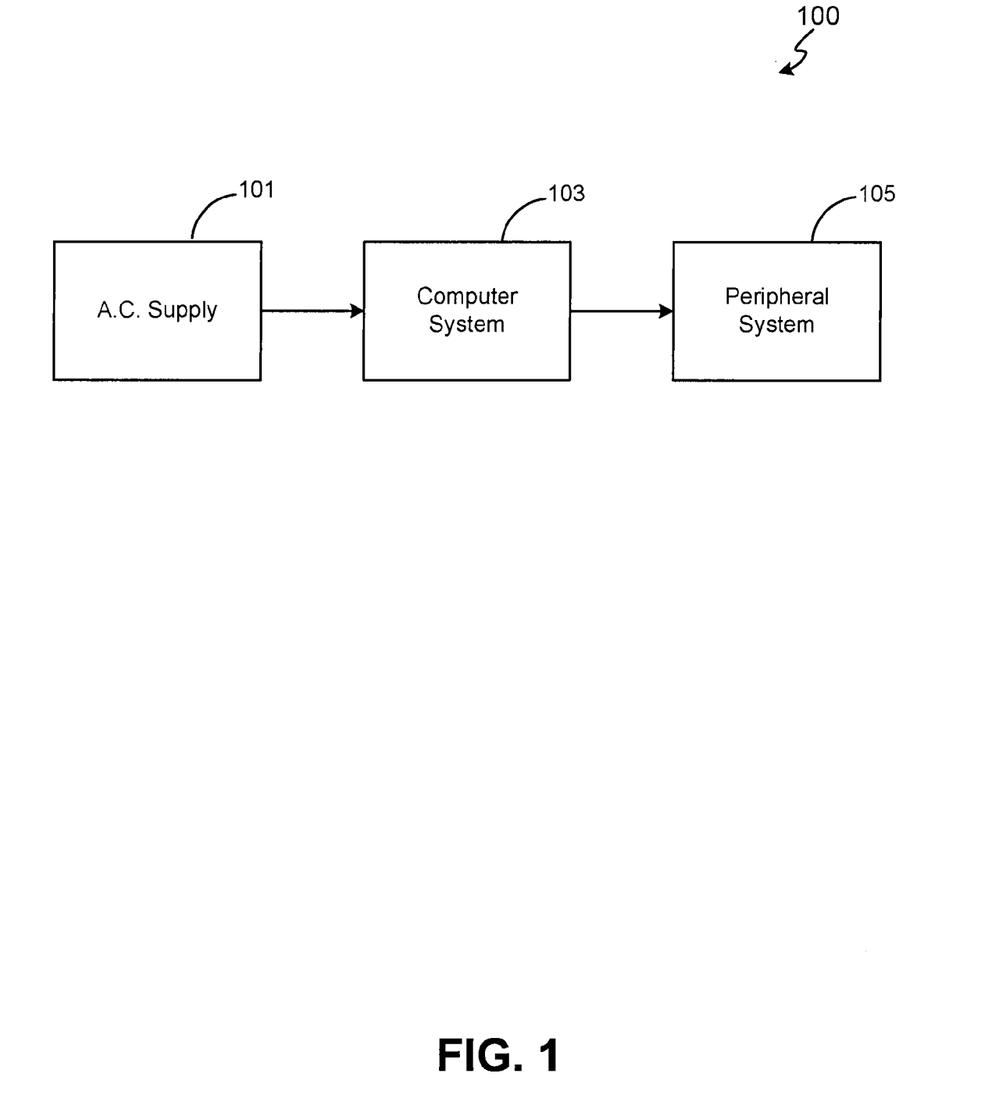
FIG. 1 is a block diagram of an exemplary system for enhancing electrical safety of peripheral systems in accordance with an exemplary embodiment of the present invention.

In accordance with various aspects of the present invention, a method and system for enhancing computer peripheral safety is provided. For example, in accordance with an exemplary embodiment, with reference to FIG. 1, an exemplary system 100 comprises an A.C. supply 101, a host computer system 103, and a peripheral subsystem or device 105 connected to host computer system 103. A.C. supply 101 suitably comprises an A.C. main supply or any other A.C. power source for supplying electrical power to equipment. Host computer system 103 is coupled to A.C. supply 101 and can comprise portable, laptop and/or notebook computers, desktop computers or any other host or operating computer configuration for operating peripheral subsystems and/or devices. Peripheral subsystem 105 can comprise any peripheral system or device, such as an ultrasound imaging and/or therapy peripheral system or device. For example, peripheral subsystem 105 can comprise systems and devices such as described in U.S. Pat. No. 6,440,071, entitled "Peripheral Ultrasound Imaging System", and hereby incorporated by reference. A host-peripheral communication link 106 can be operatively coupled between host computer 103 and peripheral subsystem 105 to facilitate control of peripheral subsystem 105, and can comprise any communication link or mechanism used between computers and peripheral devices for supplying power and/or communications. For example, communication link 106 can comprise a medical application link, such as for operatively coupling medical imaging and/or imaging/therapy systems to computer systems. To facilitate computer peripheral safety, system 100 further comprises an isolation subsystem configured for monitoring and/or isolating the A.C. supply 101 from peripheral subsystem 105.

Figure 2A:
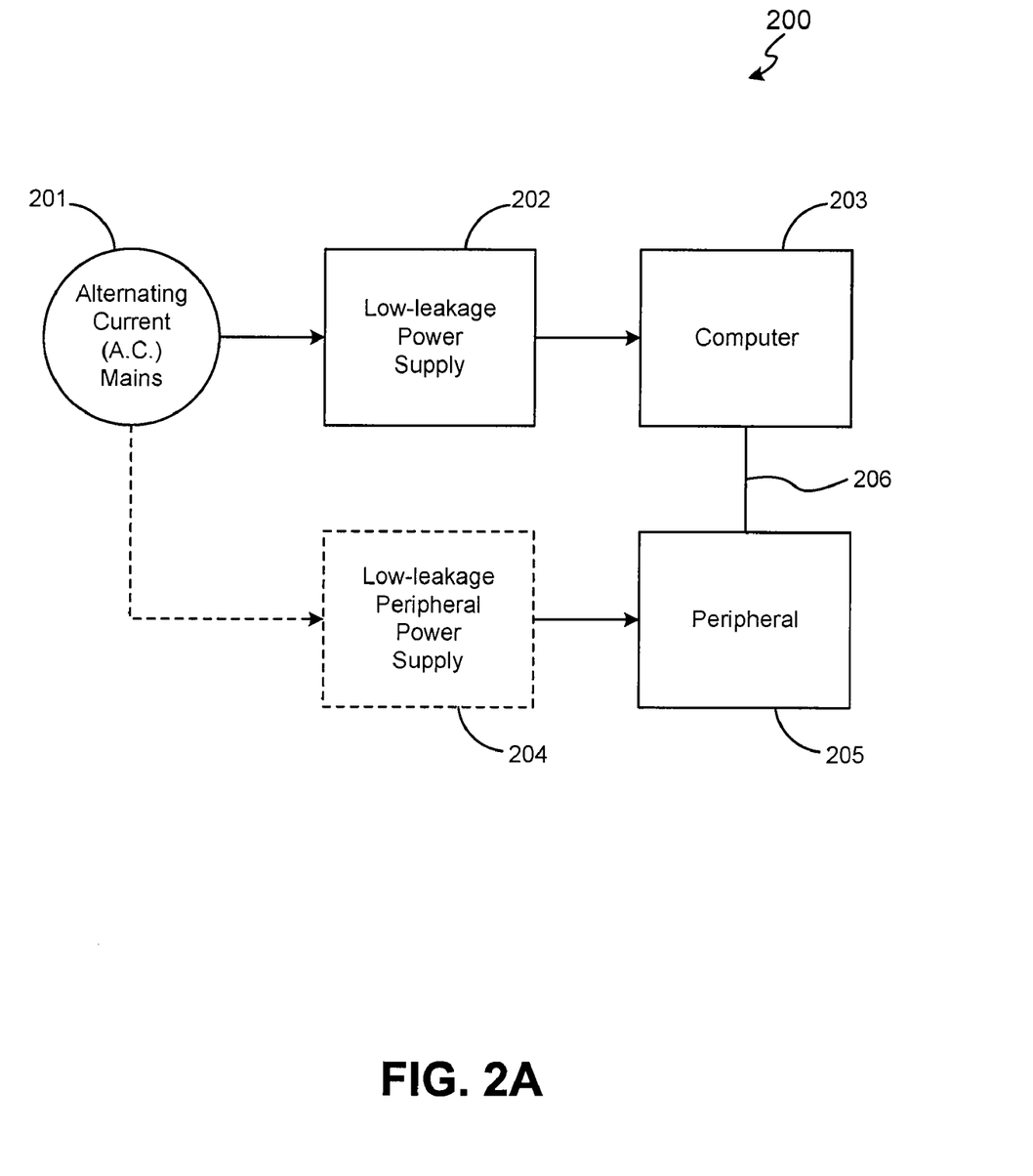
FIGS. 2A and 2B are block diagrams of a host computer, peripheral subsystem, power supplies and alternating current (A.C.) main supply for use with an isolation subsystem in accordance with an exemplary embodiment of the present invention.
Figure 2B:
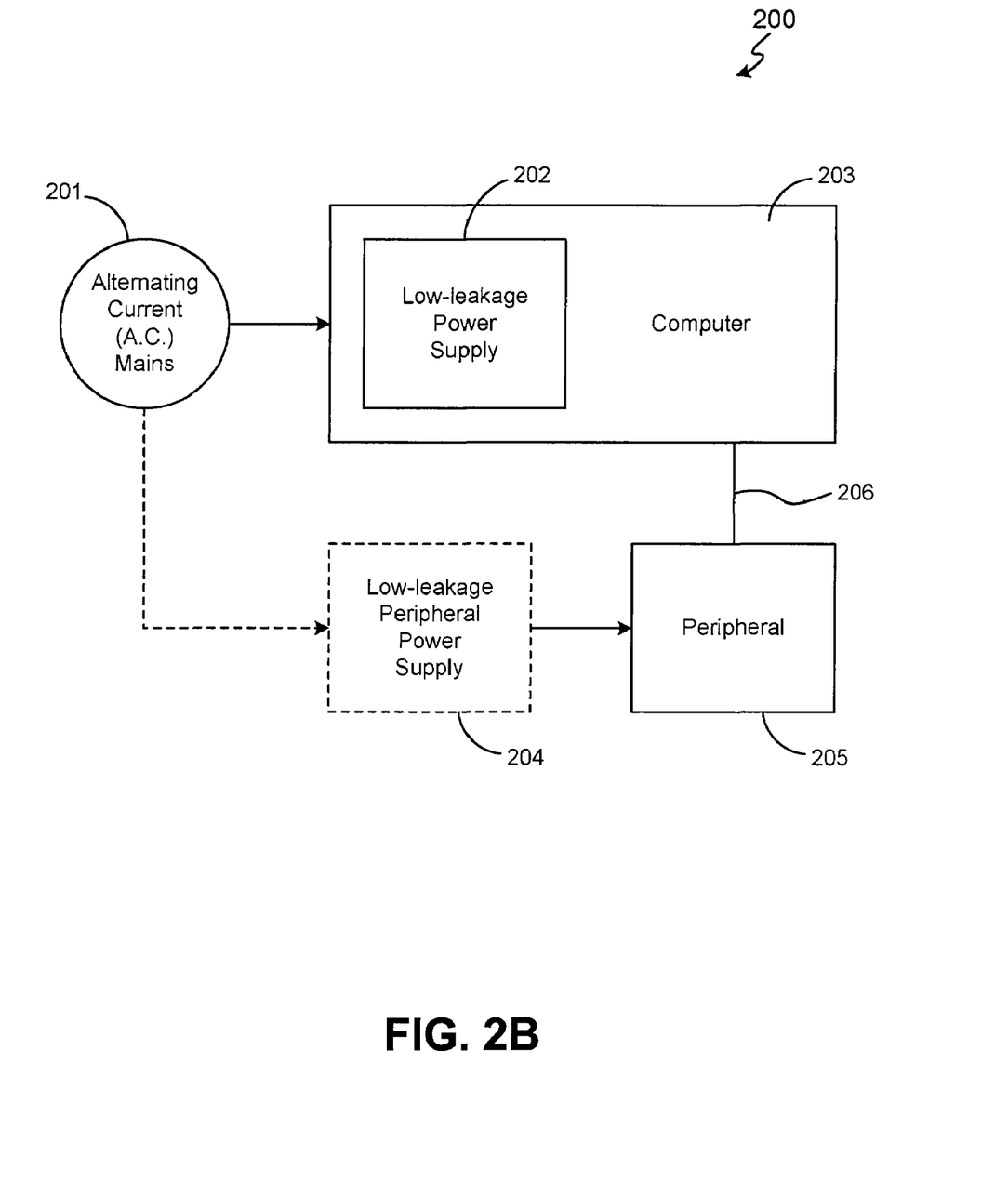

System 100 and components, A.C. supply 101, host computer 103 and peripheral 105, can be configured in various manners with an isolation subsystem for enhancing the safety of peripheral 105. For example, in accordance with an exemplary embodiment of the present invention, with reference to FIG. 2A, a peripheral safety system 200 can comprise a laptop or notebook computer 203 powered via a low-leakage/medical-grade power supply 202 that may also include a battery-backup system, including battery charger, or other uninterruptible power supply mechanism for host computer 203. Low-leakage/medical-grade power supply 202 can be suitably powered from A.C. main supply 201. In addition, an optional low-leakage/medical-grade peripheral power supply 204, powered from A.C. main supply 201, can also be coupled to peripheral 205 when additional power is needed for peripheral 205 and cannot be provided via communication link 206. Low leakage/medical-grade power supply 202 refers to a power supply or source of power which satisfies electric safety standards such as low-leakage, grounding, dielectric isolation, resistance to high potential voltages and transients. With reference to FIG. 2B, instead of laptop or notebook computers, host computer 203 can suitably comprise a desktop-style host computer and associated software 203. Typically desktop-style systems 203 differ from notebook-style systems in that power supply 202 is normally contained within the enclosure of computer 203.

An isolation subsystem can also be configured in various manners for monitoring and/or isolating A.C. supply 201 from peripheral subsystem or device 205. For example, to facilitate computer peripheral safety, a high degree of electrical isolation in one or both power supplies 202 and 204 can be provided, thus enhancing patient safety.

Figure 3:
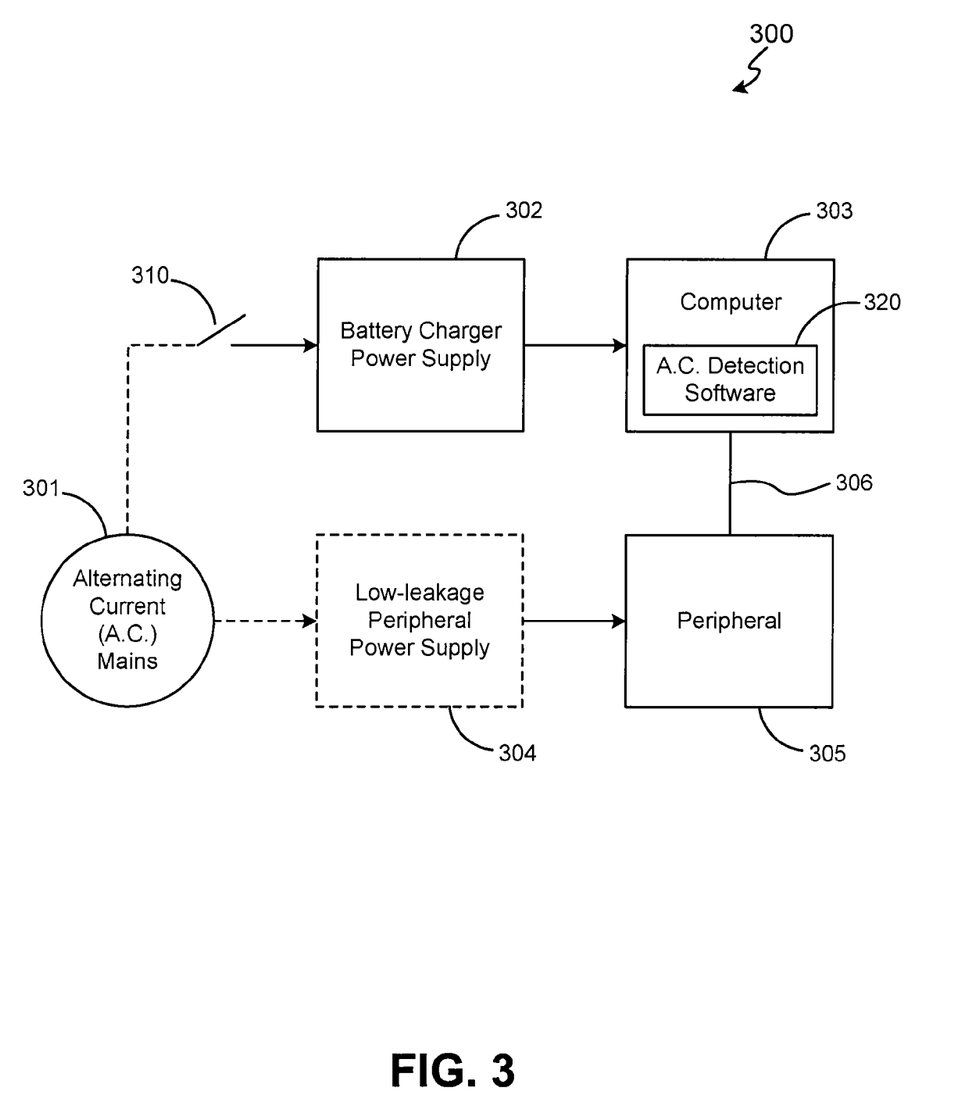
FIG. 3 is a block diagram of an exemplary system for enhancing electrical safety of peripheral systems with an isolation subsystem comprising A.C. detection software module in accordance with an exemplary embodiment of the present invention.

In accordance with another exemplary embodiment, with reference to FIG. 3, a peripheral safety system 300 can comprise a computer host and associated software 303 with an isolation subsystem comprising an A.C. detection software component 320. In this exemplary embodiment, host computer 303 is suitably powered via computer power supply/battery charger 302, powered from A.C. main 301. Power supply/battery charger 302 is configured to charge batteries for supplying an isolated power source to host computer 303. A.C. detection software component 320 is configured to detect through input devices 310 when PC battery charger 302 is connected to the A.C. main supply 301 (an unisolated power source) or disconnected (wherein an isolated power source comprising the charged battery supplies power) to the A.C. main supply 301 and disables (or re-enables) peripheral 305, e.g., disable or re-enable a medical application's functions. A.C. detection software component 320 can comprise any software and/or hardware configuration, including various input/output signals and components, for detecting when an A.C. supply is providing the source of power to host computer 303, e.g., detecting when a battery charger is connected and/or disconnected to A.C. main 301, and for suitably disabling one or more peripheral application functions, or otherwise for providing suitable warnings or other recommendations to the system user. By disabling at least some software/peripheral functionality, a high degree of electrical isolation is realized, and thus the patient safety is enhanced in medical applications.

Figure 4A:
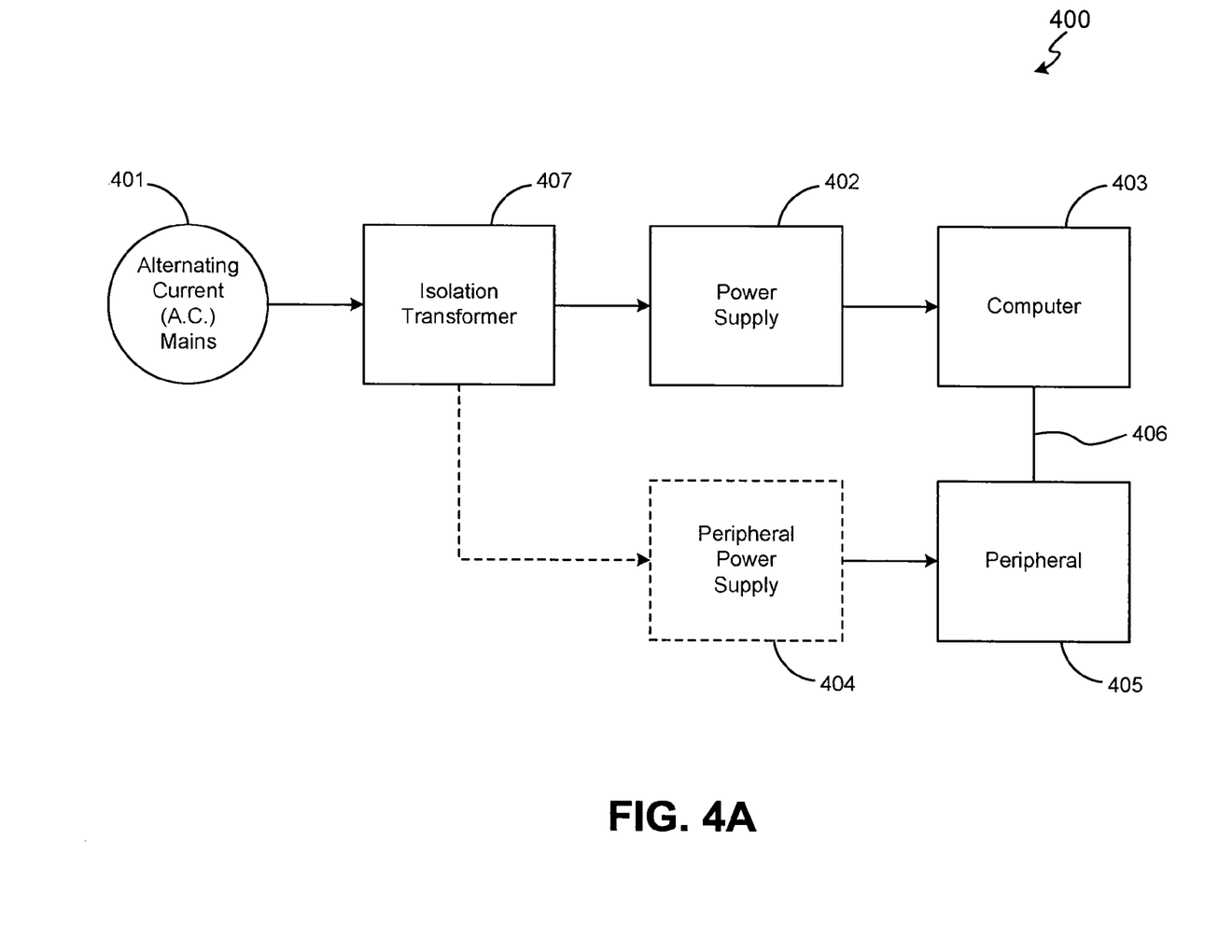
FIGS. 4A and 4B are block diagrams of exemplary systems for enhancing electrical safety of peripheral systems with an isolation subsystem and an isolation transformer in accordance with an exemplary embodiment of the present invention.
Figure 4B:
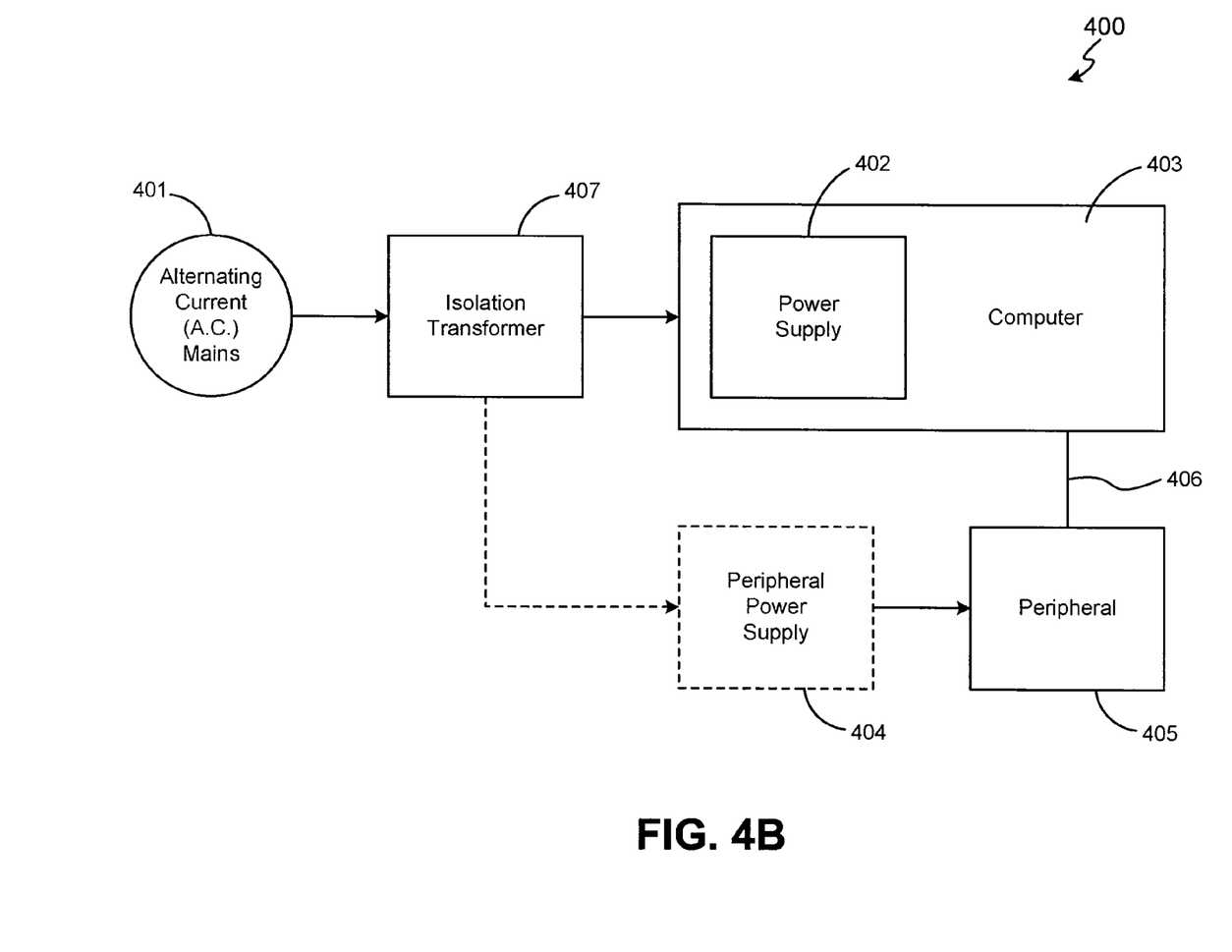

A.C. detection module 320 can be configured in addition to other isolation equipment and devices for facilitating safety. For example, with reference to FIGS. 4A and 4B, A.C. detection software can be resident within a laptop or notebook computer (FIG. 4A) or a desktop computer (FIG. 4B), with computer 403 further coupled to or including a power supply 402 coupled to an isolation transformer 407. Isolation transformer 407 can comprise any transformer configuration for isolating A.C. supplies from electrical equipment, such as computers and peripherals.

Figure 5A:
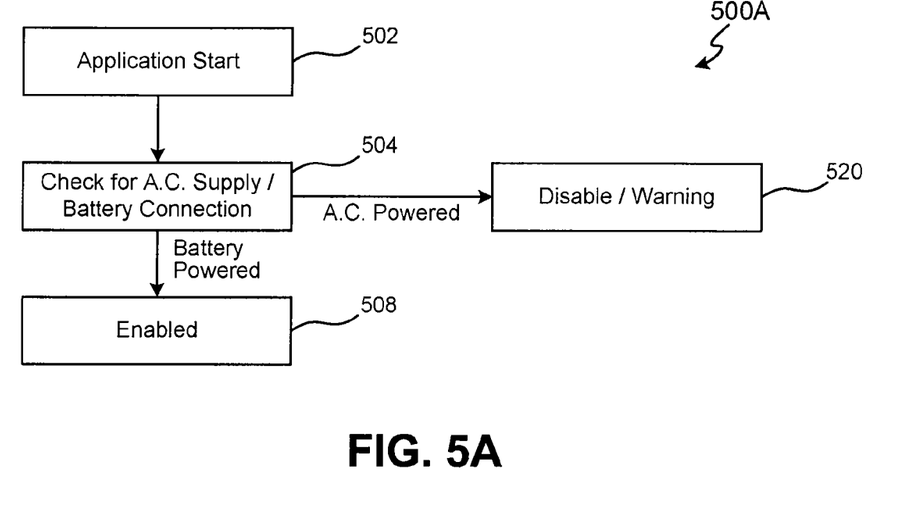
FIGS. 5A and 5B are flowcharts of operation for exemplary A.C. detection software modules in accordance with an exemplary embodiment of the present invention.

Detection module 320 can be provided in various operational steps through use of one or more algorithms and/or input/output devices for providing a method for enhancing computer peripheral safety. For example, with reference to FIG. 5A, in accordance with an exemplary embodiment, an exemplary method 500A may comprise A.C. detection module configured into application software and associated modules. As soon as the application software initiates or starts 502, the detection module checks for operative connection to an unisolated power source, e.g., an A.C. supply, or to an isolated power source, e.g., battery power 504. If not battery powered (i.e., if powered by or otherwise operatively connected to the A.C. supply, such as through the battery charger) the detection module moves to disabling functions and/or displaying a warning 520. However, if detection module determines the host computer is powered directly by battery power (e.g., the batter charger is not plugged in to the A.C. supply) 506, all normal hardware and software functionality is enabled 508, and the system continues operating.

Figure 5B:
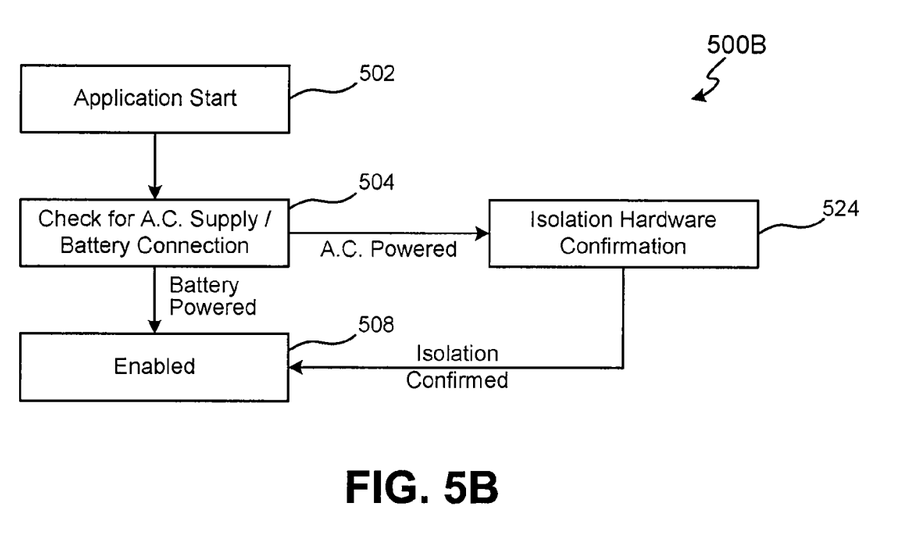

In accordance with another exemplary embodiment, with reference to FIG. 5B, instead of disabling functions or warning the system user to terminate use of any peripheral devices if a connection to the A.C. main supply is detected 520, the application software and associated modules request confirmation from the system user that isolation hardware is being used 524. If the system user confirms that appropriate isolation hardware is installed and operating, any normal hardware and software functionality is enabled 508, and usage of the peripheral device is allowed; if isolation hardware is not in place or operating, then peripheral device usage is disallowed. Such a confirmation 524 can be manually confirmed by the system user, and/or through input/output devices configured to determine the presence of isolation hardware, such as isolation transformers and devices.

Figure 6:
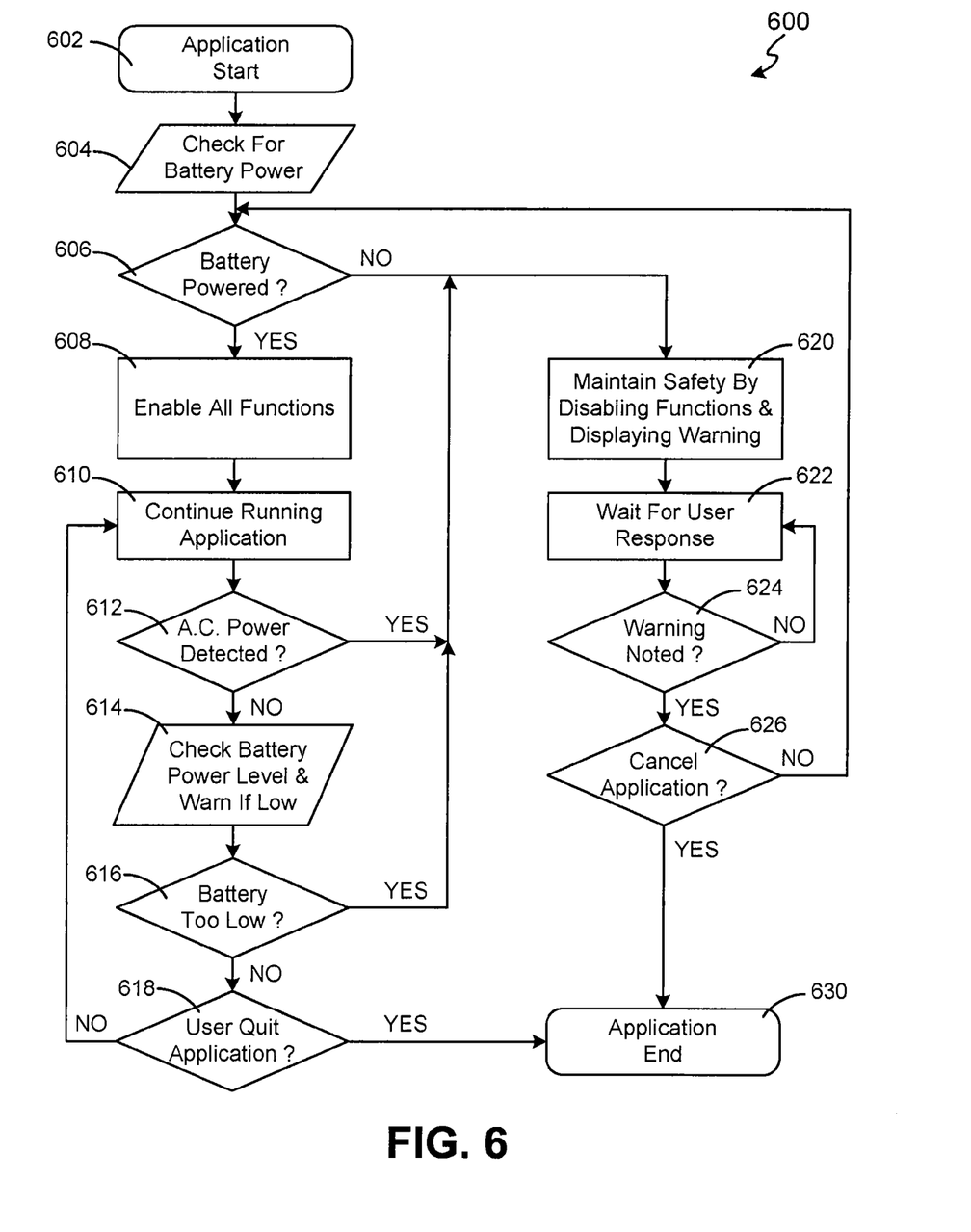
FIG. 6 is a flowchart of a A.C. detection software module in accordance with another exemplary embodiment of the present invention.

With reference to FIG. 6, another exemplary method may comprise additional monitoring and/or isolation functions. For example, as soon as the application software initiates or starts 602, the detection module checks for operative connection to an unisolated power supply, e.g., the A.C. supply, or to an isolated power supply, e.g., to battery power 604. If not battery powered (e.g., if powered by A.C. supply) the detection module moves to disabling functions and/or displaying a warning 620. However, if the detection module determines the host computer is powered directly by battery supply (e.g., the batter charger is not plugged in to the A.C. supply) 606, all normal hardware and software functionality is enabled 608, and the system continues operating or running 610 while the presence of A.C. charging is constantly scanned for by the detection module 612, e.g., the presence of A.C. charging is constantly scanned in the detection software and/or detected instantly via operating system interrupts, such as power change broadcast messages. Thereafter, if the connection to A.C. power is detected, the detection module moves to disabling functions and/or displaying a warning 620. However, if no such detection occurs, the detection module also checks whether the battery level has gone low. If the battery supply level is low, a warning can be issued to the user 614. If the battery level goes too low, e.g. almost empty, the detection module can also resort to disabling functions 620 to maintaining safety, and/or the user can request to quit the application 618 and end operation 630, or to continue the application running 610.

The process of disabling/warning 620 maintains safety by disabling functions (hardware and/or software), displaying a warning, and/or waiting for a user acknowledgement 622 if a connection to A.C. power is detected or the battery is very low or nearly empty. For example, as a warning is acknowledged 624, the user can be given the option to cancel the application 626 and thereby ending 630; if the user decides not to cancel operation, the detection module can continue with monitoring/re-checking for battery power 606. Thus, the system functionality in which safety and patient isolation is essential can be controlled such that the functionality is not re-enabled until the system is confirmed to be supplied on battery power. Such a configuration can allow the user to perform some functions, such as saving images or other processes, while safety-critical features and patient isolation can be preserved.

Figure 7A:
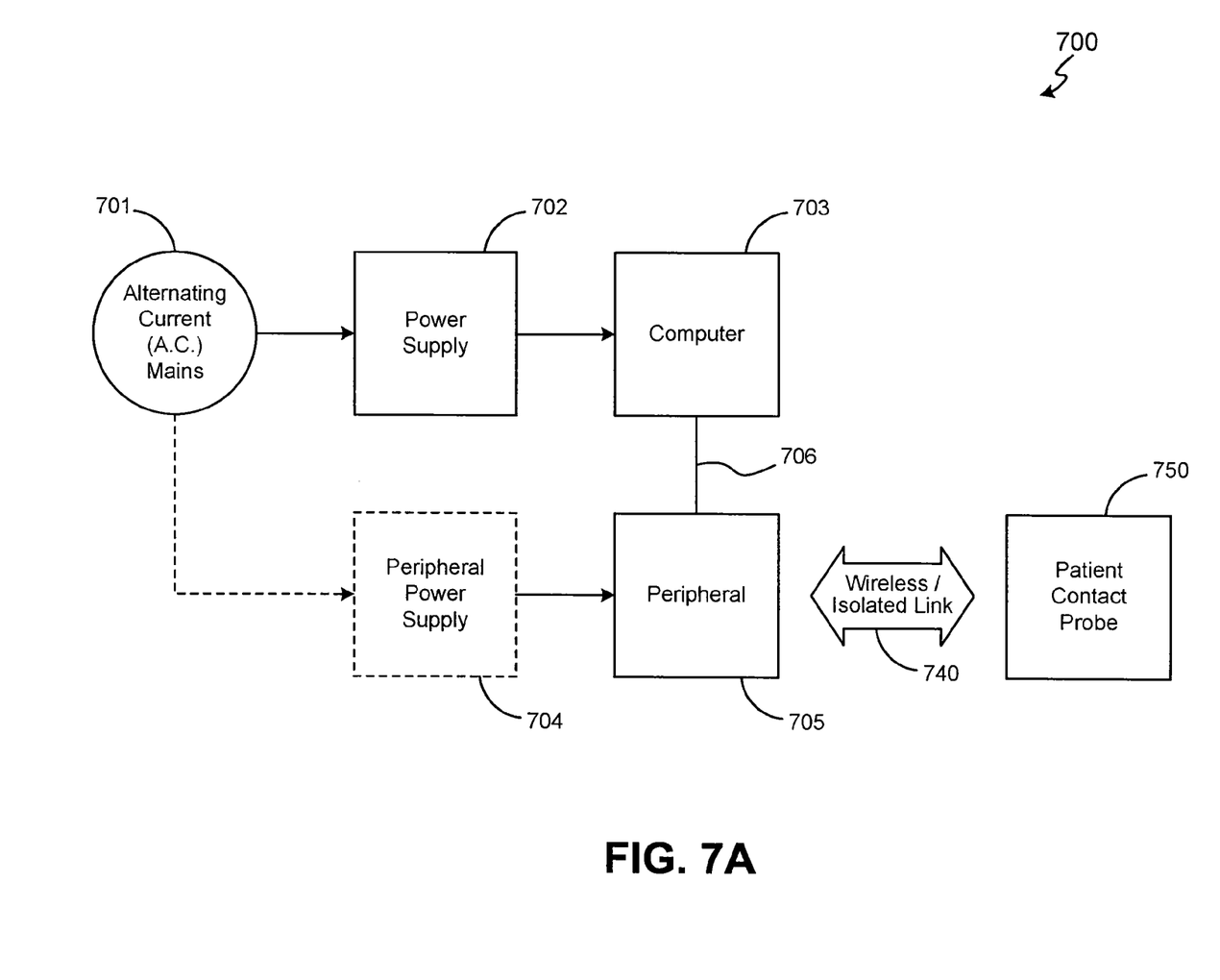
FIGS. 7A and 7B are block diagrams of exemplary systems for enhancing electrical safety of peripheral systems with an isolation subsystem comprising a wireless or other isolated link to a patient contact probe in accordance with an exemplary embodiment of the present invention.
Figure 7B:
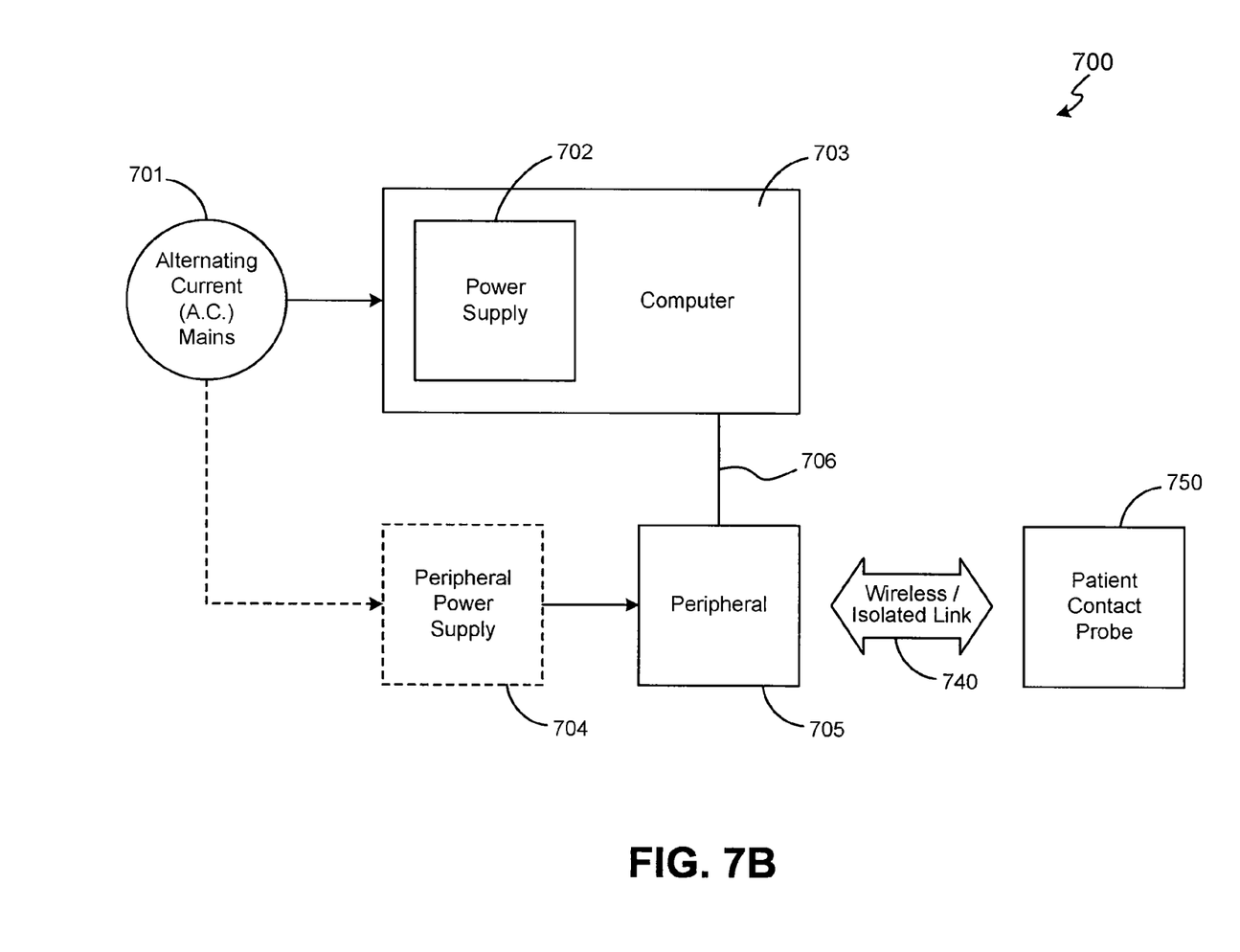

In accordance with another exemplary embodiment, with reference to FIGS. 7A (laptop or portable PC) and 7B (desktop PC), peripheral safety system 700 can include an isolation subsystem comprising a wireless and/or other isolated electrical link 740 coupled between a peripheral system 705 and a peripheral device 750, such as a patient contact probe. Some examples of wireless and/or other isolated electrical links include wireless USB (wireless Universal Serial Bus), certified wireless USB, wireless Ethernet or IEEE 802.11 based technology, Wi-Fi, WiMedia, Bluetooth, proprietary radio transceivers and associated technology, cellular or other radio network based wireless, and optical wireless such as IrDA. By providing a wireless and/or electrically safe or low-leakage isolated link 740 between the peripheral/computer and patient contact probe 750, patient safety is enhanced. Isolated link 740 may be provided at any suitable point within system 700. For example, components, part or whole, of computer 703 and/or peripheral 705 may be disposed on either side of isolated link 740, so long as a high degree of isolation between A.C. main supply 701 and patient are maintained.

Figure 8A:
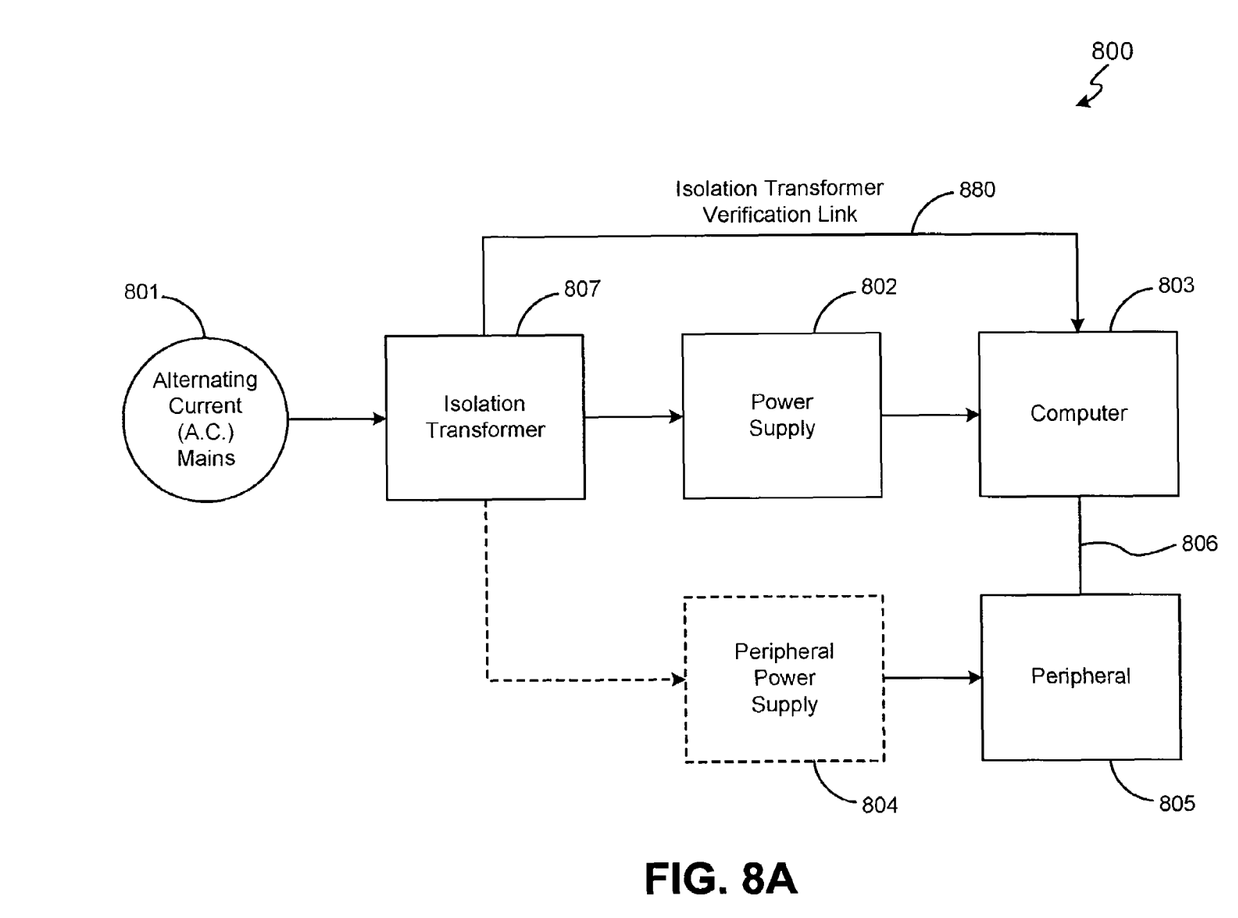
FIGS. 8A and 8B are block diagrams of exemplary systems for enhancing electrical safety of peripheral systems with an isolation subsystem comprising an isolation transformer verification link in accordance with an exemplary embodiment of the present invention.
Figure 8B:
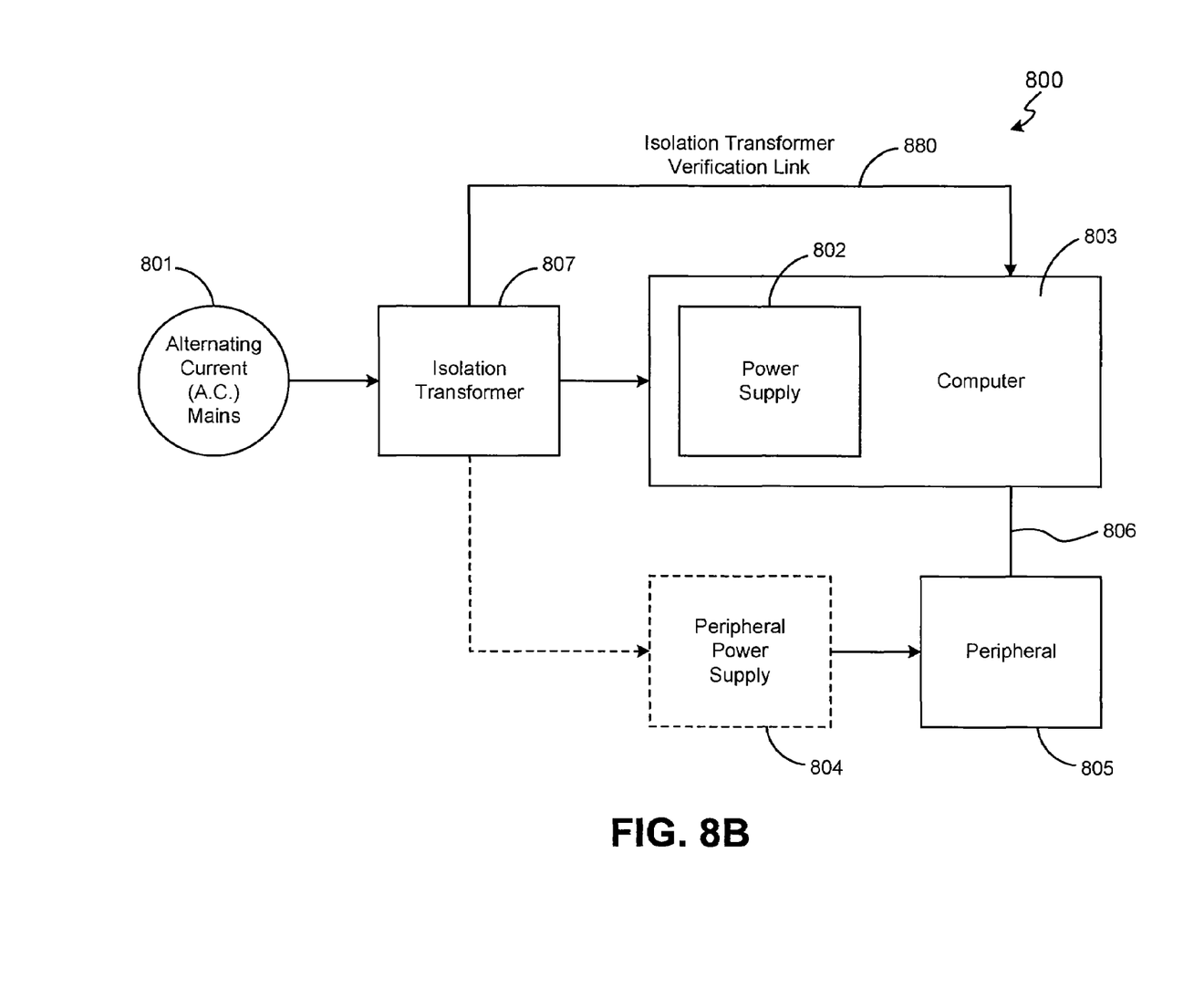

In accordance with another exemplary embodiment of the present invention, with reference to FIGS. 8A (laptop or portable PC) and 8B (desktop PC), a peripheral safety system 800 can include an isolation subsystem comprising an isolation transformer 807 configured with an isolation transformer verification link 880 configured in between isolation transformer 807 and computer 803. Isolation transformer 807 can comprise a low-leakage medical-grade isolation transformer or other like systems. As such, isolation transformer 807 provides a high degree of electrical isolation only when it is used as intended, thus isolation transformer verification link 880 is configured to confirm with computer 803 and/or peripheral 805 that isolation transformer 807 is present and in proper use. Isolation transformer verification link 980 suitably comprises a feedback mechanism that can contain software and/or hardware functionality and protection keys to assure that isolation transformer 807 and/or other components in system 800 are being used in the appropriate configuration to maintain safety. Isolation transformer verification link 880 can comprise any feedback configuration configured to monitor an isolation transformer and/or other electrical or control components and/or any of the appropriate operations of peripheral device 805. For example, in accordance with an exemplary embodiment, isolation transformer verification link 880 can comprise a wire or other coupling device connected into a USB port of computer 803 from isolation transformer 807 to allow monitoring of transformer operation. However, isolation transformer verification link 880 can comprise any other communication link, e.g., cable and/or wireless.

The present invention has been described above with reference to various exemplary embodiments. However, those skilled in the art will recognize that changes and modifications may be made to the exemplary embodiments without departing from the scope of the present invention. For example, the various operational steps, as well as the components for carrying out the operational steps, may be implemented in alternate ways depending upon the particular application or in consideration of any number of cost functions associated with the operation of the system, e.g., various of the steps may be deleted, modified, or combined with other steps. For example, although the exemplary embodiments illustrate one configuration for an isolation subsystem, it should be noted that various exemplary embodiments for an isolation subsystem can also comprise a combination of detection module and isolation transformer and/or wireless/isolated links. These and other changes or modifications are intended to be included within the scope of the present invention, as set forth in the following claims.

The invention claimed is:

1. A treatment system configured for enhanced computer peripheral safety for use with medical devices, said treatment system comprising:
   an A.C. main power supply;
   a host computer system configured with a power supply, said host computer system further coupled to said A.C. main power supply;
   a peripheral system coupled to said host computer system and configured for control of medical devices; and
   an isolation subsystem configured for isolating said A.C. power supply from said peripheral system during operation of said peripheral system, wherein said isolation subsystem comprises a detection module configured within said host computer system for monitoring supply of power from said A.C. power supply to said host computer system, wherein said detection module is configured to provide warnings to a user to allow for disabling of at least one function of said peripheral system when said A.C. power supply is supplying power to said host computer system.

2. The system according to claim 1, wherein said power supply of said host computer further comprises an A.C. powered battery charger and an isolated battery, and wherein said detection module is configured to determine whether said A.C. power supply is supplying power through said battery charger or whether said isolated battery is supplying power to said host computer system.

3. The system according to claim 2, wherein said detection module is further configured to monitor power levels of said isolated battery and provide at least one of a disabling function and a warning function to a user if said power levels are below acceptable levels.

4. The system according to claim 1, wherein said isolation subsystem further comprises an isolation transformer configured between said power supply of said host computer system and said A.C. power supply.

5. The system according to claim 1, wherein said isolation subsystem further comprises a low-leakage power supply configured between said peripheral system and said A.C. power supply.

6. The system according to claim 1, wherein said isolation subsystem comprises a wireless/isolated electrical link coupled between a medical peripheral device and said A.C. power supply.

7. The system according to claim 6, wherein said wireless/isolated electrical link is connected between said medical peripheral device and said peripheral system.

8. The system according to claim 1, wherein said isolation subsystem comprises an isolation transformer and a verification link, each configured between said A.C. power supply and said host computer.

9. The system according to claim 8, wherein said isolation transformer comprises a low-leakage, medical-grade isolation transformer.

10. A treatment system configured for enhanced computer peripheral safety for use with medical devices, said treatment system comprising:
    an A.C. main power supply;
    a host computer system configured with a power supply, said host computer system further coupled to said A.C. main power supply;
    a peripheral system coupled to said host computer system and configured for control of medical devices; and
    an isolation subsystem configured for isolating said A.C. power supply from said peripheral system during operation of said peripheral system, wherein said isolation subsystem comprises a detection module configured within said host computer system for monitoring supply of power from said A.C. power supply to said host computer system, wherein said detection module is configured to confirm with a user whether isolation hardware is operable prior to disabling of at least one function of said peripheral system when said A.C. power supply is supplying power to said host computer system.

11. A treatment system configured for enhanced computer peripheral safety for use with medical devices, said treatment system comprising:
    an A.C. main power supply;
    a host computer system configured with a power supply, said host computer system further coupled to said A.C. main power supply;
    a peripheral system coupled to said host computer system and configured for control of medical devices; and
    an isolation subsystem configured for isolating said A.C. power supply from said peripheral system during operation of said peripheral system wherein said isolation subsystem comprises a detection module configured within said host computer system for monitoring supply of power from said A.C. power supply to said host computer system, wherein said isolation subsystem comprises an isolation transformer and a verification link, each configured between said A.C. power supply and said host computer, wherein said verification link comprises a feedback mechanism configured to monitor operations of at least one of isolation transformer and said peripheral system.

12. The system according to claim 11, wherein said verification link comprises a wired connection from said isolation transformer to a USB port of said host computer.

13. A computer-implemented method for enhancing computer peripheral safety for use with medical applications, said computer-implemented method comprising:
    determining whether a host computer is being powered by an isolated power source or by an unisolated power source comprising an A.C. power supply;
    providing at least one of a disabling function to a peripheral system and a warning function to a peripheral system user if said host computer is powered by the A.C. power supply; and
    continuing operation of said peripheral system if said host computer is powered by the isolated power source, wherein said method further comprises monitoring power levels of said isolated power source and providing at least one of a disabling function and a warning function to a user if said power levels are below acceptable levels.

14. A computer-implemented method for enhancing computer peripheral safety for use with medical applications, said computer-implemented method comprising:
    determining whether a host computer is being powered by an isolated power source or by an unisolated power source comprising an A.C. power supply;
    providing at least one of a disabling function to a peripheral system and a warning function to a peripheral system user if said host computer is powered by the A.C. power supply; and
    continuing operation of said peripheral system if said host computer is powered by the isolated power source, wherein said method initially provides said warning function to a user and waits for acknowledgement before disabling any functions within said peripheral system.

15. A computer-implemented method for enhancing computer peripheral safety for use with medical applications, said computer-implemented method comprising:
- determining whether a host computer is being powered by an isolated power source or by an unisolated power source comprising an A.C. power supply;
- providing at least one of a disabling function to a peripheral system and a warning function to a peripheral system user if said host computer is powered by the A.C. power supply; and
- continuing operation of said peripheral system if said host computer is powered by the isolated power source, wherein said method confirms with a user whether isolation hardware is operable before disabling any functions within said peripheral system.

16. A peripheral isolation system configured for enhancing safety with a medical peripheral device when used with an A.C. power supply, said peripheral isolation system comprising: an isolation subsystem coupled between the A.C. power supply and the medical peripheral device, said isolation subsystem configured to perform at least one of monitoring and isolating the A.C. power supply during operation of the medical peripheral device, wherein said isolation subsystem comprises a detection module configured within a host computer system for monitoring supply of power from the A.C. power supply to the host computer system, and configured to disable at least one function of the medical peripheral device when the A.C. power supply is supplying power to the host computer system, wherein said detection module is further configured to provide warnings to a user prior to disabling of at least one function of said medical peripheral device when the A.C. power supply is supplying power to the host computer system.

17. A peripheral isolation system configured for enhancing safety with a medical peripheral device when used with an A.C. power supply, said peripheral isolation system comprising: an isolation subsystem coupled between the A.C. power supply and the medical peripheral device, said isolation subsystem configured to perform at least one of monitoring and isolating the A.C. power supply during operation of the medical peripheral device, wherein said isolation subsystem comprises a detection module configured within a host computer system for monitoring supply of power from the A.C. power supply to the host computer system, and configured to disable at least one function of the medical peripheral device when the A.C. power supply is supplying power to the host computer system, wherein said detection module is further configured to determine whether an isolated battery is supplying power to said host computer system, and is configured to monitor power levels of the battery and provide at least one of a disabling function and a warning function to a user if the power levels are below acceptable levels.

18. A peripheral isolation system configured for enhancing safety with a medical peripheral device when used with an A.C. power supply, said peripheral isolation system comprising: an isolation subsystem coupled between the A.C. power supply and the medical peripheral device, said isolation subsystem configured to perform at least one of monitoring and isolating the A.C. power supply during operation of the medical peripheral device, wherein said isolation subsystem comprises a detection module configured within a host computer system for monitoring supply of power from the A.C. power supply to the host computer system, and configured to disable at least one function of the medical peripheral device when the A.C. power supply is supplying power to the host computer system, wherein said isolation subsystem comprises a wireless/isolated electrical link coupled between the medical peripheral device and the A.C. power supply.

19. A peripheral isolation system configured for enhancing safety with a medical peripheral device when used with an A.C. power supply, said peripheral isolation system comprising: an isolation subsystem coupled between the A.C. power supply and the medical peripheral device, said isolation subsystem configured to perform at least one of monitoring and isolating the A.C. power supply during operation of the medical peripheral device, wherein said isolation subsystem comprises a detection module configured within a host computer system for monitoring supply of power from the A.C. power supply to the host computer system, and configured to disable at least one function of the medical peripheral device when the A.C. power supply is supplying power to the host computer system, wherein said isolation subsystem comprises an isolation transformer and a verification link, each coupled between the A.C. power supply and the host computer, and wherein said verification link comprises a feedback mechanism configured to monitor operations of at least one of the isolation transformer and the medical peripheral device.

20. A method for enhancing computer peripheral safety for use with medical applications, said method comprising:
- providing an isolation subsystem coupled between an A.C. power supply and a medical peripheral device;
- performing at least one of monitoring and isolating the A.C. power supply during operation of the medical peripheral device;
- determining in a host computer whether the host computer is being powered by a battery or by the A.C. power supply;
- providing a warning function to a peripheral system user if the host computer is powered by the A.C. power supply; and
- continuing operation of the medical peripheral device if the host computer is powered by the battery.

21. The method according to claim 20, wherein said method further comprises providing a wireless/isolated electrical link coupled between the medical peripheral device and the A.C. power supply.

22. The method according to claim 20, wherein said method further comprises providing an isolation transformer coupled between the A.C. power supply and a host computer, and providing a verification link comprising a feedback mechanism configured to monitor operations of at least one of the isolation transformer and the medical peripheral device.

* * * * *